United States Patent [19]

Akita et al.

[11] Patent Number: 5,003,043
[45] Date of Patent: Mar. 26, 1991

[54] PEPTIDES REPRESENTING EPITOPIC SITES FOR THE MAJOR HTLV-I ENVELOPE PROTEIN, ANTIBODIES THERETO, AND USES THEREOF

[75] Inventors: Robert W. Akita, Oakland; Dagne L. Florine, Moraga; John S. Ralston, San Ramon, all of Calif.

[73] Assignee: Triton Biosciences Inc., Alameda, Calif.

[21] Appl. No.: 198,416

[22] Filed: May 25, 1988

[51] Int. Cl.$^5$ .......................... C07K 7/10; C07K 7/00
[52] U.S. Cl. .................................... 530/324; 530/325; 530/326; 530/327; 530/328
[58] Field of Search ............... 530/326, 324, 350, 325, 530/328, 327; 435/68.1, 7

[56] References Cited

U.S. PATENT DOCUMENTS

| | | | |
|---|---|---|---|
| 4,525,300 | 6/1985 | Yoshida et al. | 530/326 |
| 4,661,445 | 4/1987 | Saxinger et al. | 435/7 |
| 4,663,436 | 5/1987 | Elder et al. | 530/324 |
| 4,722,888 | 2/1988 | Broder et al. | 435/68.1 |

FOREIGN PATENT DOCUMENTS

84/03564  9/1984  PCT Int'l Appl. .

OTHER PUBLICATIONS

Bromberg, Chem. Abs. 104(13), 107522q, 1985.
Tanaka et al, Chem Abs. 104(13), 10754u, 1986.
Virology, 36, 338-347, 1984, Halton et al, "Identification of Gag and Env. Gene Products of HTLV".
Proc. Nat'l. Acad. Sci., vol. 81, 6202-6206, 1984, Kiyokawa, "Envelope Proteins of HTLV: Expression in E. coli".
Virology, 132, 1-11, 1984, Schneider et al, "Sera from ATLV Patients React with Env. and Core Polypeptides of ATLV".
Proc. Natl. Acad. Sci., vol. 81, pp. 3856-3860, 6/84, Coligan et al., "HTLV Associated Membrane Antigens".
P. J. Fischinger et al., "Current Status and Strategies for Vaccines Against Diseases Induced by Human T-Cell Lymphotropic Retroviruses (HTLV-I, -II, -III)", Cancer Research (Suppl.), 45:4694s-4699s (1985).
S. B. Kanner et al., "Human Retroviral Env and Gag Polypeptides: Serologic Assays to Measure Infection", J. of Immunology 137(2): 674-;678 (1986).
T. D. Copeland, "Envelope Proteins of Human T Cell Leukemia Virus Type I: Characterization by Antisera to Synthesize Peptides and Identification of a Natural Epitope, " J. of Immunology 137(9): 2945-2951 (1986).
H. Shida et al., "Effect of the Recombinant Vaccinia Viruses That Express HTLV-I Envelope Gene on HTLV-I Infection", The EMBO Journal 6(11): 3379-3384 (1987).
E. S. Kleinerman et al., "A Synthetic Peptide Homologous to the Envelope Proteins of Retroviruses Inhibits Monocyte-Mediated Killing by Inactivating Interleukin 1", J. of Immunology 139(7): 239-2337 (1987).
H. Nakamura, "Protection of Cynomolgus Monkeys Against Infection by Human T-Cell Leukemia Virus Type-I by Immunization with Viral Env Gene Products Produced in *Escherichia coli*", Int. J. Cancer 40: 403-407 (1987).
T. J. Palker et al., "Mapping of Immunogenic Regions of Human T-Cell Leukemia Virus Type I (HTLV-I) gp46 and gp21 Envelope Glycoproteins with Env-Encoded Synthetic Peptides and a Monoclonal Antibody to gp46", J. of Immunology 142(3): 971-978 (1989).

*Primary Examiner*—John Doll
*Assistant Examiner*—T. D. Wessendorf
*Attorney, Agent, or Firm*—Shelley Precivale; Al Jecminek; Karen Babyak Dow

[57] ABSTRACT

The present invention discloses synthetic peptides and antibodies raised thereto wherein the synthetic peptides represent important epitopic sites recognized by the 0.5 α antibody, a human monoclonal antibody which can neutralize HTLV-I. Also, the uses of these peptides or antibodies thereto either alone or in combination with peptides representing the epitopic site for the predominant antibodies found in HTLV-I env seropositive sera as diagnostics, therapeutics and vaccines are disclosed.

6 Claims, 3 Drawing Sheets

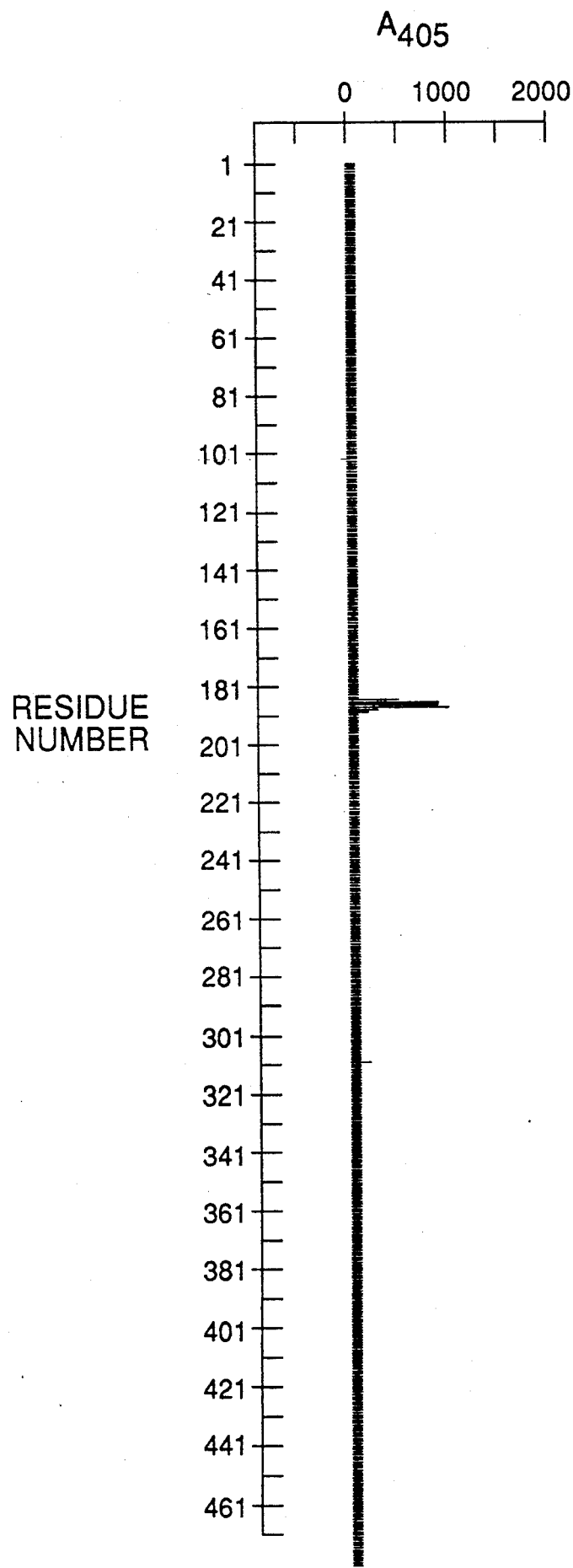
FIG._1

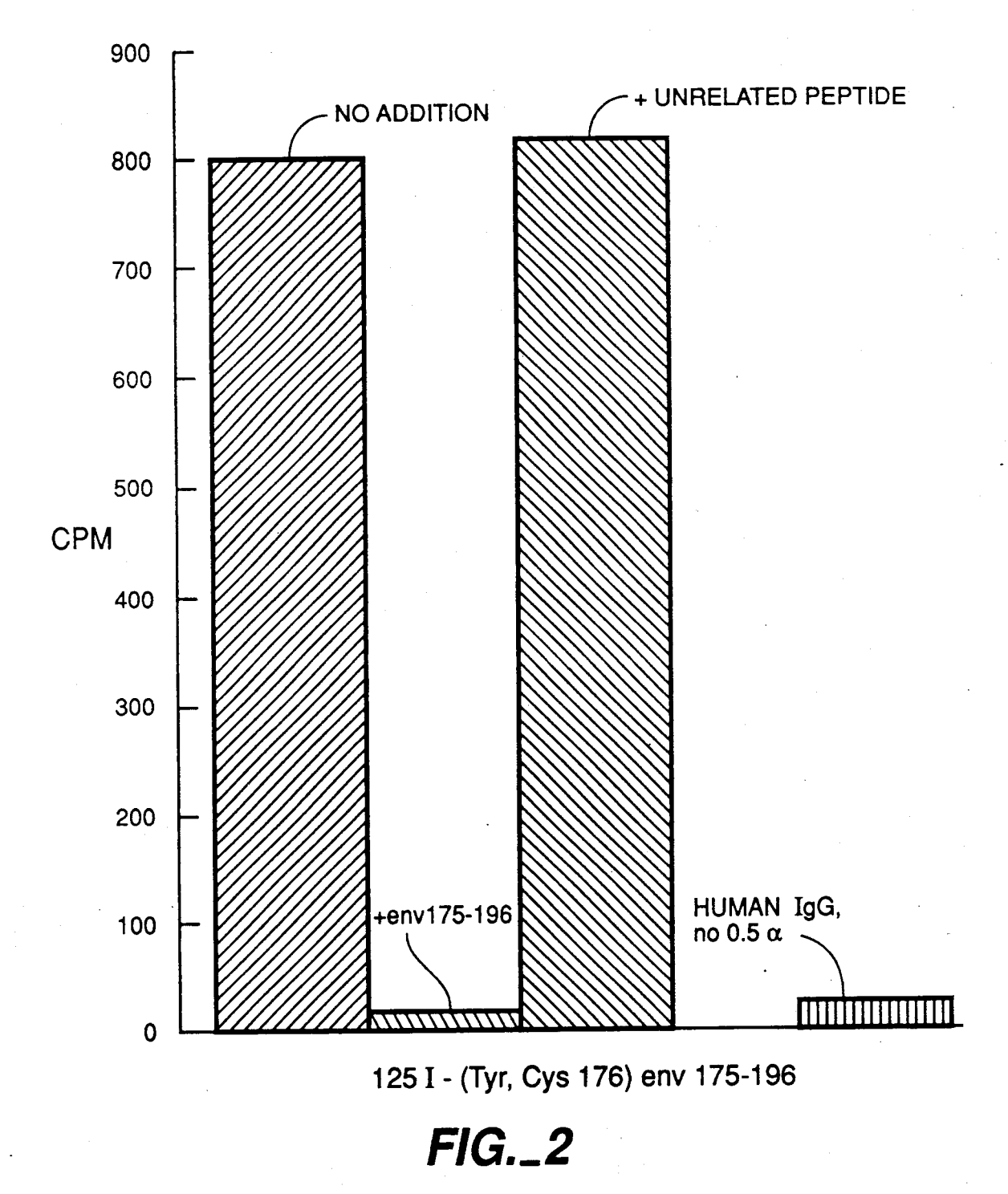

FIG._2

1  2  3  4  5
FIG._3

PEPTIDES REPRESENTING EPITOPIC SITES FOR THE MAJOR HTLV-I ENVELOPE PROTEIN, ANTIBODIES THERETO, AND USES THEREOF

BACKGROUND OF THE INVENTION

The human T-cell leukemia viruses (HTLV) comprise a family of exogenous human retroviruses. HTLV type-I (HTLV-I) is etiologically associated with adult T-cell leukemia-lymphoma (ATL), first described clinically in Japan and found endemic to southern Japan, the Caribbean Basin, and certain parts of Africa. HTLV type II (HTLV-II) was isolated from a patient with a T-cell variant of hairy cell leukemia. Despite divergence between HTLV-I and HTLV-II, they are conserved to the extent that they are serologically cross-reactive. A third subgroup of HTLV (HTLV-III or HIV) refers to a virus isolated from patients with acquired immune deficiency syndrome (AIDS).

Specific antibodies to HTLV-I have been detected in ATL patients and in asymptomatic carriers; and in patients with tropical spastic paraparesis and with HTLV-I associated myelopathy. These antibodies are known to recognize both gag and env protein of the virus. Viral gag proteins have been purified, sequenced, and murine monoclonal antibodies against these core proteins (p19, P24) have been produced and extensively used for detecting core antigens. Murine monoclonal antibody to a minor component of envelope protein (gp 21 or p20E) has been reported. Recently, a monoclonal antibody (mAb) designated 0.5α has been produced to the major component (gp46) of the envelope glycoprotein (env). (See U.S. Pat. No. 4,722,888). Antibody from the cell line 0.5α, described in U.S. Pat. No. 4,722,888, binds specifically to the major HTLV-I envelope protein (gp 46). However, the specific epitopic site for binding of the antibodies secreted by cell line 0.5α has not been reported previously.

SUMMARY OF THE INVENTION

The present invention discloses synthetic peptides representing important epitopic sites on the major HTLV-I envelope protein including the sites recognized by the 0.5α antibody. Another aspect of this invention discloses antibodies having binding affinity for the peptides of the invention. A third aspect of this invention includes a peptide composition containing a combination of peptides which exhibit specific binding to a predominant class of antibodies found in HTLV-I env seropositive sera and the novel peptides recognized by the 0.5α antibody described above. The peptides and antibodies of this invention may be useful in diagnosing the presence of HTLV-I infection in humans, they may be used as therapeutic agents in the treatment of HTLV-I-associated diseases, they may be used as vaccines against HTLV-I infection, or they may be used as prognostic indicators after HTLV-I infection.

DESCRIPTION OF THE DRAWINGS

FIG. 1 is a plot of the absorbance obtained in the antibody-binding ELISA vs. the number of the N-terminal amino acid of each 8-mer peptide within the sequence of HTLV-I env.

FIG. 2 illustrates the binding of 0.5α mAb to the synthetic peptide [Tyr$^{175}$, Cys$^{176}$]env175-196.

FIG. 3 illustrates the inhibition of 0.5α mAb binding to HTLV-I env by [Tyr$^{175}$, Cys$^{176}$]env175-196.

DESCRIPTION OF THE PREFERRED EMBODIMENT

Broder, et al. (U.S. Pat. No. 4,722,888) recently produced a human monoclonal antibody reactive against the major envelope glycoprotein of human T-cell leukemia virus type I (HTLV-I). The mAb 0.5α is capable of binding to the surface membrane of HTLV-I producing cells and thereby activating complement mediated lysis of HTLV-I infected cells. It is known that the 0.5α mAb binds the 46 gp env protein in humans infected with HTLV-I, although the specific binding sites or regions are unknown. The present invention identifies the specific epitope or epitopes to which the 0.5α mAb binds. These epitopes were discovered using the Geysen method of epitope mapping which involves multiple peptide synthesis on activated polyethylene rods (Geysen, H. M., Meloen, R. H., and Barteling, S. J. [1984] *Proc. Natl. Acad. Sci USA* 81, 3998–4002). The Geysen method provides for simultaneous synthesis of hundreds of peptides which can then be assayed for antibody binding. Based on the amino acid sequence deduced from the nucleotide sequence for the proviral genome of HTLV-I, 481 peptides were synthesized by moving one amino acid at a time through the sequence of the 61 kd precursor envelope glycoprotein of HTLV-I. The peptides synthesized were then reacted with 0.5α mAb to determine binding between them. The results are shown in FIG. 1. The first class of peptides of this invention are those that bind to 0.5α having at least the following sequence:

$$X\text{-}AA_1\text{-}AA_2\text{-}AA_3\text{-}Leu\text{-}Pro\text{-}AA_4\text{-}Y \quad (I)$$

where X is an amino acid sequence up to 13 amino acids long, selected in sequence from the following sequence:

$$\text{Phe-Leu-Asn-Thr-Glu-Pro-Ser-Gln-Leu-Pro-Pro-Thr-Ala-;} \quad (X)$$

Y is an amino acid sequence up to 14 amino acids long, selected in sequence from the following sequence:

$$\text{-Ser-Asn-Leu-Asp-His-Ile-Leu-Glu-Pro-Ser-Ile-Pro-Trp-Lys;} \quad (Y)$$

AA$_1$ is Pro or Ile;
AA$_2$ is Pro, Ala, Glu, Gly, His, Ile, Leu, Gln, Arg, Ser, Thr, or Val;
AA$_3$ is Leu or Ile; and
AA$_4$ is His, Gly, Leu, Asn, Gln, Arg or Trp.
More preferably:
AA$_1$ is Pro or Ile;
AA$_2$ is Pro, Val, or Ile;
AA$_3$ is Leu or Ile; and
AA$_4$ is His, Trp or Gly.
More preferably the peptides of this invention are one of the following sequences:

$$X\text{-Pro-Pro-Leu-Leu-Pro-His-Y} \quad (IA)$$

where X and Y are defined the same as for formula I above. Most preferably the peptides are one of the following sequences:

$$\text{Gln-Leu-Pro-Pro-Thr-Ala-Pro-Pro-Leu-Leu-Pro-His;} \quad (IB)$$

$$\text{Glu-Pro-Ser-Gln-Leu-Pro-Pro-Thr-Ala-Pro-Pro-Leu-Leu-Pro-His-Ser; or} \quad (IC)$$

Asn-Thr-Glu-Pro-Ser-Gln-Leu-Pro-Pro-Thr-Ala-
Pro-Pro-Leu-Leu-Pro-His-Ser-Asn     (ID)

Most preferably the peptides of this invention are those found between residues 177–196 of HTLV-I env (gp46) and having at least the sequence of any of formulas I-ID above. Depending on the end use of the peptides of this invention, it may be necessary to stabilize or modify the peptides by any means known in the art of protein chemistry. Also, longer peptides are contemplated as part of this invention by adding additional amino acids from the HTLV-I env sequence. Another aspect of this invention is the antibodies raised to and having binding affinity for the peptides of formulas I-ID above.

A second class of peptides has been identified as another epitope for recognition by a predominant antibody in HTLV-I env seropositive sera. This peptide is found between residues 281–320 of HTLV-I env precursor. It is defined by the formula:

Ile-Gln-Ala-Ile-Val-Ser-Ser-Pro-Cys-His-Asn-Ser-Leu-Ile-Leu-Pro-Pro-Phe-Ser-Leu-Ser-Pro-Val-Pro-Thr-Leu-Gly-Ser-Arg-Ser-Arg-Arg-Ala-Val-Pro-Val-Ala-Val-Trp-Leu (II)

The Peptides of formula II or antibodies raised to and having binding affinity for the peptides of formula II can be used in combination with the peptides or antibodies of formulas I-ID above to form novel cocktails for diagnosing or treating HTLV-I or for vaccinating against HTLV-I infection.

The peptides of the present invention can be prepared by conventional processes for synthesizing peptides; more specifically, using processes as described in Schroder and Lubke, *The Peptides*, Vol. 1, published by Academic Press, New York (1966), or Izumiya, et al., *Synthesis of Peptides*, published by Maruzen Publishing Co., Ltd., (1975), both of which are herein incorporated by reference.For example, an azide process, an acid chloride process, an acid anhydride e process, a mixed anhydride process, a DCC process, an active ester process (for example: p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The peptides of the present invention are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. (Amino groups that are not being used in the coupling reaction must be protected to prevent coupling at an incorrect location.)

In case that a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin; hydroxymethyl resins, phenol resins, tert-alkyloxycarbonylhydrazidated resins, and the like.

An amino group-protected amino acid is bound in sequence through condensation of its reactive carboxyl group to the terminal amino group of the growing chain. After synthesizing the complete sequence, the peptide is split off from the insoluble carrier to produce the peptide. This solid-phase approach is generally described by Merrifield, et al. in J. Am. Chem. Soc., 85, 2149–2156 (1963), which is herein incorporated by reference.

In the foregoing process, it is preferred that respective amino acids of histidine, tyrosine, glutamic acid, lysine, serine, cysteine, threonine, and aspartic acid be protected at the side chain functional groups. These functional groups at the side chain are protected with ordinary protective groups which are split off after completion of the reaction. The functional groups that take part in the reaction are generally activated.

Examples of protective groups for amino groups include: benzyloxycarbonyl, Boc, tert-amyloxycarbonyl, isobornyloxycarbonyl, p-methoxybenzyloxycarbonyl, Cl-Z, adamantyloxycarbonyl, trifluoroacetyl, phthalyl, formyl, o-nitrophenylsulfenyl, diphenylphosphinothioyl, and the like.

Examples of protective groups for the imino group of histidine include: Tos, Bzl, benzyloxycarbonyl, trityl, and the like.

Examples of protective groups for the hydroxy group of tyrosine include: Bzl, $Cl_2$-Bzl, BrZ, benzyloxycarbonyl, acetyl, Tos, and the like.

Examples of protective groups for the amino group of lysine include: benzyloxycarbonyl, Cl-Z, $Cl_2$-Bzl, Boc, Tos, and the like.

Protection for the carboxyl groups of glutamic acid and aspartic acid includes: esterification of the carboxylic acids with benzyl alcohol, methanol, ethanol, tert-butanol, and the like.

Examples of protective groups for the hydroxy of serine include: Bzl, tert-butyl, and the like.

Examples of protective groups for threonine include: O-benzyl, O-tert-butyl, and the like.

Examples of protective groups for cysteine include: paramethoxybenzyl, acetamideomethyl, S-trityl, S-butyl, and the like.

Examples of activated carboxyl groups include: the corresponding acid chlorides, acid anhydrides, mixed acid anhydrides, azides, and active esters (esters with pentachlorophenol, p-nitrophenol, N-hydroxysuccinimide, N-hydroxybenzotriazole, N-hydroxy-5-norbornene-2,3dicarboxydiimide, and the like).

The peptides of this invention can also be prepared through DNA techniques. The amino acid sequence of the desired peptide is used to deduce the codon sequence for the single-stranded DNA. synthesized using conventional synthetic techniques (including multiple gene copy techniques), then the double-stranded DNA is prepared and inserted at a suitable site in a cloning vehicle, vector, or plasmid. An appropriate organism, such as bacteria cells, yeast cells, or mammalian cells, is transformed to obtain expression of the desired peptide.

The prepared peptides of the present invention can be isolated and purified from the reaction mixture by means of peptide separation, for example, by extraction, counter-current distribution, column chromatography, high performance liquid chromatography, and the like.

The peptides of this invention form salts with a variety of inorganic or organic bases. The non-toxic, pharmaceutically-acceptable salts are preferred, although other salts are also useful in isolating or purifying the product. Such pharmaceutically-acceptable salts include metal salts, such as sodium, potassium, or lithium, alkaline earth metal salts, such as calcium or magnesium, and salts derived from amino acids, such as arginine or lysine. The salts are obtained by reacting the acid form of the peptide with an equivalent of the base supplying the desired ion in a medium in which the salt precipitates or in aqueous medium and then lyophilizing.

Similarly, the peptides form salts with a variety of inorganic and organic acids. Again, the non-toxic, pharmaceutically-acceptable salts are preferred, although other salts are also useful in isolating or purifying the product. Such pharmaceutically-acceptable salts include those formed with hydrochloric acid, methanesulfonic acid, sulfuric acid, maleic acid, and the like. The salts are obtained by reacting the product with an equivalent amount of the acid in a medium in which the salt precipitates.

As noted above, antibodies raised against the peptides of the invention are also an important aspect of this invention. For example, antibodies or antibody fragments, e.g., F(ab')$_2$ or Fab fragments, against the peptides of formulas I-IC may be useful in therapy as anti-HTLV-I agents and as binding components in immunoassays to detect HTLV-I infection in humans. Accordingly, to facilitate the production of antibodies according to the invention the peptides of the invention are preferably treated or prepared in a fashion which optimizes their antigenicity.

Antigenic peptides can be prepared by using the peptides or fragments of the peptides of the present invention as haptens and reacting the peptides or fragments with a suitable carrier in the presence of a hapten-carrier binding agent. In this case, natural and synthetic proteins having a high molecular weight, which are conventionally employed in the preparation of antigens, can be employed as carriers to be bound to the haptens. Examples of such carriers include: albumins of animal sera, globulins of animal sera, thyroglobulins of animals, hemoglobulins of animals, hemocyanins of animals, such as Keyhole limpet hemocyamin (KLH), proteins extracted from ascaris, polylysine, polyglutamic acid, lysine-glutamic acid copolymers, and copolymers containing lysine or ornithine.

As hapten-carrier binding agents, those conventionally employed in the preparation of antigens can be employed. Specific examples of these agents include: diazonium compounds for cross linking aromatic residues, aliphatic dialdehydes for cross linking an amino group with an amino group, dimaleimide compounds for cross linking a thiol group with a thiol group, maleimidocarboxyl-N-hydroxysuccinimide esters for cross linking an amino group with a thiol group, and agents used in conventional peptide bond forming reactions in which amide bonds are formed from an amino group and a carboxyl group. Also as the hapten-carrier binding agent, it is also possible to use diazonium aryl carboxylic acids, such as p-diazonium phenylacetic acid, in combination with conventional peptide bond-forming agents, such as the dehydrating and condensing agents described above.

The coupling reaction for preparing the antigenic forms of the peptides of the present invention is suitably carried out in an aqueous solution or a conventional buffer solution having a pH of 7 to 10, preferably in a buffer solution having a pH of 7.5 to 9, at temperatures of about 0° to 40° C., preferably around room temperature.

The coupling reaction is generally completed within about 1 to about 24 hours, preferably 3 to 5 hours. Representative examples of buffer solutions which can be used in the above process include:

0.2N sodium hydroxide-0.2M boric acid-0.2M potassium chloride buffer solution;

0.2M sodium carbonate-0.2M boric acid-0.2M potassium chloride buffer solution;

0.05M sodium tetraborate-0.2M boric acid-0.05M sodium chloride buffer solution; and 0.1M dihydrogen potassium phosphate-0.05M sodium tetraborate buffer solution.

Proportions of the hapten, hapten-carrier binding agent, and carrier can be appropriately determined, but it is preferred that the molar ratio of hapten to carrier be about 20 to about 1 and the molar ratio of binding agent to hapten be about 10 to about 1. In the coupling reaction, the carrier is bound to the hapten via the hapten-carrier binding agent to obtain a desired antigen composed of a peptide-carrier complex.

After completion of the coupling reaction, the antigen can easily be isolated and purified by means of dialysis, gel filtration, fractional precipitation, and the like.

The antibody or antibodies of the present invention which are raised to a peptide or peptides of this invention, can be monoclonal or polyclonal, but monoclonal is preferred. In general, antibodies may be obtained by injecting the desired immunogen or antigen into a wide variety of vertebrates in accordance with conventional techniques. Suitable vertebrates include mice, rats, rabbits, sheep, and goats, with mice being preferred. Usually, the animals are bled periodically with the successive bleeds having improved titer and specificity. The antigens may be injected intramuscularly, intraperitoneally, subcutaneously, or the like. Chimeric antibodies (mouse human hybrids) made by genetic engineering are also contemplated by this invention.

Polyclonal antibodies are prepared by hyperimmunization of the animal with antigen. Then the blood of the animal is collected shortly after the repeated immunizations and the gamma globulin is isolated. Suitable methods for preparing polyclonal antibodies are described in the *Handbook of Experimental Immunology*, 3d edition, (ed. Weir, 1978), which is herein incorporated by reference.

To obtain monoclonal antibodies, spleen cells from the immunized vertebrate demonstrating the desired antibody response are immortalized. The manner of immortalization is not critical, but the most common method is fusion with a myeloma fusion partner. Other techniques of immortalization include EBV transformation, transformation with bare DNA, such as oncogenes or retroviruses, or any other method which provides for stable maintenance of the cell line and production of monoclonal antibodies. The general process for obtaining monoclonal antibodies is described by Kohler and Milstein, in *Nature*. 256, 495–497 (1975), which is herein incorporated by reference. Human monoclonal antibodies may be obtained by fusion of the spleen cells with an appropriate human fusion partner, such as WI-L2, described in European Application No. 82.301103.6, the relevant portions of which are herein incorporated by reference. A detailed technique for producing mouse×mouse monoclonal antibodies is taught by Oi and Herzenberg, in *Selected Methods in Cellular Immunology*, 351–372 (eds. Mishell and Shiigi, 1980), which also is herein incorporated by reference. The resulting hybridomas are screened to isolate individual clones, each of which secretes a single antibody species to the antigen.

The peptides and/or antibodies may be used without modification or may be modified in a variety of ways, for example, by labeling. Labeling is intended to mean joining, either covalently or non-covalently, a moiety which directly or indirectly provides for a means of detection. A wide variety of labels are known and include: radionuclides, enzymes, substrates, cofactors, inhibitors, fluorescers, chemiluminescers, magnetic particles, and the like.

Many of the techniques for linking the peptides to suitable labels involve the use of activated carboxyl groups, either through the use of carbodiimide or active esters to form peptide bonds; the formation of thioethers by reaction of a mercapto group with an activated halogen, such as chloroacetyl: or activated olefin, such as maleimide, or the like.

The peptides and antibodies of this invention may be used to diagnose HTLV-I infection. Since the peptides of this invention define epitopes which are not common to HTLV-II or III, the peptides of this invention, or antibodies thereto, may also be used in differential diagnosis. In particular, the peptides of the invention can be used to detect the presence of antibodies which are produced by HTLV-I infected individuals. Antibodies of the invention can be used to detect the existence of the major HTLV-I envelope protein in HTLV-I infected people. The peptides and antibodies of this invention may be used in the preparation of diagnostic tests, such as immunoassays. Such diagnostic techniques include, for example, enzyme immune assay (EIA), enzyme multiplied immunoassay technique (EMIT), enzyme-linked immunosorbent assay (ELISA), radioimmune assay (RIA), flourescence immune assay, either single or double antibody techniques, and other techniques where either the peptides or antibodies of this invention are labeled with some detectable tag. See generally Enzyme Immunoassay, by Maggio, CRC Press (1981). Preferably the peptides of formula I or antibodies raised thereto are used alone or in combination with the peptides of formula II or antibodies raised thereto. When used in combination the peptides or antibodies of formulas I and 11 can be used as a "cocktail" to detect simultaneously either the antibodies or epitopes of the HTLV-I virus or to provide added immunogenicity in a vaccine or therapeutic.

The peptides and antibodies of this invention can be used as a vaccine or therapeutic against the HTLV-I virus. The peptides of this invention can be used alone in straight chain or cyclic ring form, as a polymer wherein adjacent polypeptide repeating units are bonded together by oxidized cysteine residues, or as a conjugate linked to a carrier. Vaccines containing effective amounts of peptides of this invention may provide active immunity in that antibodies would be produced in sufficient amount to provide protection for the subject against HTLV-I infection. The antibodies raised to the peptides of this invention may be used to provide passive immunity by direct administration in an effective amount to the host. The immunizing composition or vaccine can be administered parenterally using any known methods. Booster injections can be given if needed. Exact doses depend on the subject to be treated and the peptide used and can be determined using known challenge techniques. Typical amounts of peptide and carrier, the specific reaction conditions for the conjugation reaction and vaccine preparation are given in Bittle et al., Nature, 298, 30-33 (July, 1982). When used as vaccines, the novel peptides of this invention may be administered directly to the host to be immunized or depending on the size of the peptides, it may be desirable to conjugate them to carrier proteins such as ovalbumin or serum albumin prior to their administration. Alternatively, nucleotide sequences corresponding to the appropriate amino acid sequence could be cloned into an expression vector which contains additional immunogenic sequence. Purified recombinant protein may then be administered directly to the host. The vaccine composition will include an immunogenic amount of the peptide, a parenteral vehicle, and, optionally, an immunopotentiator. The peptides and antibodies of this invention may be used to treat HTLV-I-associated diseases. Peptides of this invention may cause the production of antibodies that are capable of inducing lysis of HTLV-I infected cells via any of several immune pathways, such as the complement pathway or antibody dependent cell mediated cytotoxicity. Polyclonal and monoclonal antibodies raised to the peptides of this invention and injected into an HTLV-I infected person may provide passive therapy. Antibodies raised to the peptides of this invention may also be used, when coupled to a cytotoxic agent, to direct the cytotoxin to the HTLV-I infected cells thereby destroying the infected cells.

Therapeutic formulations of the novel peptides or fragments or derivatives may be administered in any conventional dosage formulation. While it is possible for the active ingredient to be administered alone, it is preferable to present it as a pharmaceutical formulation. Formulations comprise at least one active ingredient as defined above together with one or more acceptable carriers thereof and optionally other therapeutic agents. Each carrier must be "acceptable" in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy.

EXAMPLE 1

Peptide Synthesis

Reagents used in peptide synthesis were purchased from the indicated vendors: Boc amino acids, Peninsula Laboratories, Belmont, Calif.; diisopropylcarbodiimide and 1-hydroxybenzotriazole, Aldrich, Milwaukee, Wisc.; carbon-14 labelled amino acids, New England Nuclear.

All peptides were synthesized according to established Merrifield solid phase synthetic procedure (Erickson et al., (1976) Proteins 2, pp 256-527 and Stewart et al., (1984) Solid Phase Synthesis Pierce Chemical Co. Rockford Ill.) using an automated instrument, Model 9500, from Biosearch (San Rafael, Calif.). The first amino acid, i.e., the carboxy terminal residue, was esterified to choloromethylated polystyrene-divinylbenzene copolymer (Bio-Rad, 1% cross-linked, 1.34 milli-equivalents/g) as described previously in Hoeprich and Doolittle (1983) Biochemistry 22, pp 2049. Subsequent amino acids were coupled twice using diisopropylcarbodiimide as a coupling agent. In general, the Boc group was removed by treating the protected peptide resin for 20 min with 45% trifluoroacetic acid in dichloromethane (v/v), followed by two 5 min neutralizations with 5% diisopropylethylamine in dichloromethane (v/v). The resin was washed before and after each deprotection, neutralization and coupling step with appropriate solvents. Boc group removal and completeness of coupling was monitored qualitatively by a ninhydrin color test (Kaiser et al., (1970) Anal. Biochem. 34. pp 595). Carbon-14 containing amino acids, e.g., glycine, were coupled initially through a diisopropylcarbodiimide mediated reaction and secondly by utilizing a preformed 1-hydroxybenzotriazole ester.

All peptides were cleaved from the resin with simultaneous side-chain protecting group removal by exposure to anhydrous hydrogen fluoride for 40 min at 0°–4° C. in the presence of 10% anisole (v/v). After removal of hydrogen fluoride by water aspiration, the resin was washed with anhydrous ethyl ether to remove the anisole. The peptide was washed from the resin with sequential washes of dimethylformamide, 50% dimethylformamide/ 10% acetic acid, 10% acetic acid and distilled water: the combined washings were lyophilized.

Purification of the peptides was accomplished by reverse-phase high performance liquid chromatography (HPLC). Using a preparative column (Whatman, Partisil 10 ODS-3 Magnum 20, 2.2×50 cm), the desired peptide was eluted during gradient development of the chromatogram: the elution program ranged from 83% solvent A (0.05% trifluoroacetic acid/acetonitrile) to 50% A and 50% B over 65 minutes. A portion of each purified peptide was hydrolyzed in 6.0N HCL (Pierce) using a Waters "Pico-Tag" work station. Amino acid compositions were obtained by precolumn derivatization with O-phthalaldehyde followed by quantitative resolution, on reverse-phase HPLC (Henrikson and Meredith (1984) Anal. Biochem. 136 pp 65–74).

EXAMPLE 2

Binding of mAb 0.5 Alpha To Synthetic Peptides From HTLV-I Env Sequence

Using the Geysen technique of peptide synthesis described previously, 481 peptides were synthesized on polyethylene rods or "pins". Each peptide represents an 8-mer made by moving one amino acid at a time through the sequence of the 61 kd env precursor of HTLV-I. A solution of 175 μl of mAb 0.5 alpha (3.7 nM) was mixed with each of the peptide-pins overnight at 4° C. Each peptide-pin was mixed with Protein-A/horseradish peroxidase (HRP) conjugate and developed with 1mM 2,2'-Azino-bis(3-ethylbenthiazoline-6-sulfonic acid) substrate. Results are shown as vertical lines corresponding to the absorbance obtained in the antibody-binding ELISA, plotted above the number of the N-terminal amino acid of each 8-mer peptide within the sequence of HTLV-I env. This plot shows a peak of binding to amino acids at approximately 184 to 198. (See FIG. 1).

EXAMPLE 3

Reaction of mAb 0.5 Alpha With The Synthetic Peptide $^{125}$I-[Tyr$^{175}$, Cys$^{176}$]-175-196 From HTLV-I Env Sequence IODO-GEN (Pierce Chemical Co. Rockfork, Ill.) was used to label the synthetic peptide [Tyr$^{175}$, Cys$^{176}$]env175-196 (prepared according to the general procedure of Example 1) with $^{125}$I to a specific activity of approximately $1.5 \times 10^{15}$ cpm/mol. MAb 0.5 α (3.3 nM) was assayed by reacting with $^{125}$I-peptide (21 nM) in 100 μL of 50 mM sodium phosphate, 150 mM NaCl pH 7.5 (PBS) containing 1% bovine serum albumin and 1% ovalbumin. The immune complexes were precipitated with 50 μL of Pansorbin cells (Calbiochem, LaJolla, Calif.). In some experiments unlabeled peptide (8.3 μM) was added to reaction mixtures. In FIG. 2, the results of this experiment are shown. Indeed, mAb 0.5α did bind with $^{125}$I-[Tyr$^{175}$Cys$^{176}$]env175-196 and this binding was competed with unlabeled [Tyr$^{175}$, Cys$^{176}$]env175-196 but was not competed with an unrelated peptide.

EXAMPLE 4

Inhibition of mAb 0.5 Alpha Binding To E. Coli Expressed Constructs of HTLV-I Env By [Tyr$^{175}$, Cys$^{176}$]env175-196

Constructs of HTLV-I env were expressed in E. coli. Protein was extracted in Laemli sodium dodecyl sulfate (SDS) sample buffer and applied to a 12% SDS-polyacrylamide gel (Laemli, U. [1970] Nature [London] 227,680).), electrophoresed and transfered electrophoretically to nitrocellulose. The transfers were then probed with mAb 0.5 α (3.3 nM) in the presence and absence of [Tyr$^{175}$, Cys$^{176}$]env175-196 (3 μM), and an unrelated peptide. Antibody binding was detected with conjugates of Protein-A and HRP after developing with α-chloronaphtol. Samples shown were: lane 1, molecular weight standards; lane 2, no additional peptide: lane 3, plus unrelated peptide; lane 4, plus [Tyr$^{175}$, Cys$^{176}$]env175-196 and lane 5, no additional peptide. FIG. 3 shows that the [Tyr$^{175}$, Cys$^{176}$]env175-196 peptide did indeed inhibit binding of mAb 0.5α to the HTLV-I env constructs.

What is claimed is:

1. Peptides having specific binding affinity for 0.5α mAB and having the following amino acid sequence:

X-AA$_1$-AA$_2$-AA$_3$-Leu-Pro-AA$_4$-Y where X is selected from the group consisting of:
Ala-, Thr-Ala-, Pro-Thr-Ala-, Pro-Pro-Thr-Ala-, Leu-Pro-Pro-Thr-Ala-, Gln-Leu-Pro-Pro-Thr-Ala-, Ser-Gln-Leu-Pro-Pro-Thr-Ala-, Pro-Ser-Gln-Leu-Pro-Pro-Thr-Ala-, Glu-Pro-Ser-Gln-Leu-Pro-Pro-Thr-Ala-, Thr-Glu-Pro-Ser-Gln-Leu-Pro-Pro-Thr-Ala-, Asn-Thr-Glu-Pro-Ser-Gln-Leu-Pro-Pro-Thr-Ala-, Leu-Asn-Thr-Glu-Pro-Ser-Gln-Leu-Pro-Pro-Thr-Ala-, and Phe-Leu-Asn-Thr-Glu-Pro-Ser-Gln-Leu-Pro-Pro-Thr-Ala-;
Y is selected from the group consisting of:
-Ser, -Ser-Asn, -Ser-Asn-Leu, -Ser-Asn-Leu-Asp, -Ser-Asn-Leu-Asp-His, -Ser-Asn-Leu-Asp-His-Ile, -Ser-Asn-Leu-Asp-His-Ile-Leu, -Ser-Asn-Leu-Asp-His-Ile-Leu-Glu, -Ser-Asn-Leu-Asp-His-Ile-Leu-Glu-Pro-, -Ser-Asn-Leu-Asp-His-Ile-Leu-Glu-Pro-Ser, -Ser-Asn-Leu-Asp-His-Ile-Leu-Glu-Pro-Ser-Ile, -Ser-Asn-Leu-Asp-His-Ile-Leu-Glu-Pro-Ser-Ile-Pro, -Ser-Asn-Leu-Asp-His-Ile-Leu-Glu-Pro-Ser-Ile-Pro-Trp, and -Ser-Asn-Leu-Asp-His-Ile-Leu-Glu-Pro-Ser-Ile-Pro-Trp-Lys;
AA$_1$ is Pro or Ile;
AA$_2$ is Pro, Ala, Glu, Gly, His, Ile, Leu, Gln, Arg, Ser, Thr, or Val;
AA$_3$ is Leu or Ile; and
AA$_4$ is His, Gly, Leu, Asn, Gln, Arg, or Trp.

2. Peptides of claim 1 wherein:
AA$_1$ is Pro or Ile;

AA$_2$ is Pro, Val, or Ile;
AA$_3$ is Leu or Ile; and
AA$_4$ is His, Trp, or Gly.

3. The peptides of claim 1 wherein:
AA$_1$ is Pro:
AA$_2$ is Pro;
AA$_3$ is Leu; and
AA$_4$ is His.

4. The peptides of claim 1 wherein:
X is Asn-Thr-Glu-Pro-Ser-Gln-Leu-Pro-Pro-Thr-Ala-Y is -Ser-Asn;
AA$_1$ is Pro:
AA$_2$ is Pro;
AA$_3$ is Leu; and
AA$_4$ is His.

5. The peptides of claim 3 wherein:
X is Glu-Pro-Ser-Gln-Leu-Pro-Pro-Thr-Ala-; and
Y is -Ser.

6. A peptide having specific binding affinity for 0.5α mAb and having the following amino acid sequence:

Gln-Leu-Pro-Pro-Thr-Ala-Pro-Pro-Leu-Leu-Pro-His.

* * * * *